(12) United States Patent
Beeckler et al.

(10) Patent No.: US 10,828,099 B2
(45) Date of Patent: Nov. 10, 2020

(54) SPRING-LOADED BALLOON

(71) Applicant: Biosense Webster (Israel) Ltd., Yokneam (IL)

(72) Inventors: Christopher Thomas Beeckler, Brea, CA (US); Joseph Thomas Keyes, Sierra Madre, CA (US); Rowan Olund Hettel, Pasadena, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 225 days.

(21) Appl. No.: 15/895,555

(22) Filed: Feb. 13, 2018

(65) Prior Publication Data

US 2018/0168726 A1 Jun. 21, 2018

Related U.S. Application Data

(63) Continuation of application No. 14/706,058, filed on May 7, 2015, now Pat. No. 9,907,610.

(51) Int. Cl.
*A61B 18/14* (2006.01)
*A61B 18/04* (2006.01)
(Continued)

(52) U.S. Cl.
CPC ...... *A61B 18/1492* (2013.01); *A61B 17/1204* (2013.01); *A61B 17/12122* (2013.01); *A61B 17/12136* (2013.01); *A61B 18/04* (2013.01); *A61M 25/10* (2013.01); *A61M 25/104* (2013.01); *A61B 2017/00053* (2013.01); *A61B 2017/00862* (2013.01); *A61B 2018/0022* (2013.01); *A61B 2018/00172* (2013.01); *A61B 2018/00285* (2013.01); *A61B 2018/00351* (2013.01); *A61B 2018/00357* (2013.01); *A61B 2018/00577* (2013.01); *A61B 2034/2051* (2016.02); *A61B 2090/3966* (2016.02);
(Continued)

(58) Field of Classification Search
None
See application file for complete search history.

(56) References Cited

U.S. PATENT DOCUMENTS

| 6,012,457 A | 1/2000 | Lesh |
| 6,024,740 A | 2/2000 | Lesh et al. |

(Continued)

FOREIGN PATENT DOCUMENTS

| JP | 2011/520515 | 7/2011 |
| RU | 2487685 C1 | 7/2013 |

(Continued)

OTHER PUBLICATIONS

International Search Report dated Sep. 6, 2016, Application No. EP 16 16 8596.

(Continued)

*Primary Examiner* — Brian T Gedeon (57) ABSTRACT

Cardiac catheterization is conducted using a probe having a balloon assembly, in which a spring has a resting axially elongated configuration and a torsed, axially shortened configuration. A balloon is twisted about the spring and mechanically linked to the spring. A flexible sheath is disposed about the spring within the balloon, the sheath and the wall of the balloon defining a chamber to contain a fluid flowing therein and thereout of the balloon.

15 Claims, 7 Drawing Sheets

(51) Int. Cl.
    *A61B 18/00*     (2006.01)
    *A61B 17/14*     (2006.01)
    *A61B 17/12*     (2006.01)
    A61M 25/10     (2013.01)
    *A61B 17/00*     (2006.01)
    *A61B 34/20*     (2016.01)
    *A61B 90/00*     (2016.01)

(52) U.S. Cl.
    CPC ............. *A61M 2025/1068* (2013.01); *A61M 2025/1077* (2013.01); *A61M 2025/1081* (2013.01); *A61M 2025/1093* (2013.01)

(56) References Cited

U.S. PATENT DOCUMENTS

| | | | |
|---|---|---|---|
| 6,226,542 | B1 | 5/2001 | Reisfeld |
| 6,301,496 | B1 | 10/2001 | Reisfeld |
| 6,814,733 | B2 | 11/2004 | Schwartz et al. |
| 6,892,091 | B1 | 5/2005 | Ben-Haim et al. |
| 6,997,924 | B2 | 2/2006 | Schwartz et al. |
| 7,156,816 | B2 | 1/2007 | Schwartz et al. |
| 7,340,307 | B2 | 3/2008 | Maguire et al. |
| 7,536,218 | B2 | 5/2009 | Govari et al. |
| 7,756,576 | B2 | 7/2010 | Levin |
| 8,333,757 | B2 * | 12/2012 | Mazzone ........... A61M 25/1006 606/21 |
| 2009/0287203 | A1 | 11/2009 | Mazzone et al. |
| 2012/0158104 | A1 | 1/2012 | Huynh et al. |
| 2013/0197497 | A1 * | 8/2013 | Wittenberger ......... A61B 18/02 606/21 |
| 2014/0005711 | A1 | 1/2014 | Saab et al. |
| 2015/0119884 | A1 | 4/2015 | Fung et al. |

FOREIGN PATENT DOCUMENTS

| | | |
|---|---|---|
| WO | WO 2002/05868 A2 | 1/2002 |
| WO | WO 2012/058153 A1 | 5/2012 |
| WO | WO 2012/143130 A1 | 6/2012 |
| WO | WO 2012/134592 A1 | 10/2012 |

OTHER PUBLICATIONS

International Search Report dated Sep. 26, 2019, Application No. EP 19 16 8192.

Russian Search Report dated Aug. 13, 2019, Application No. 2016116802.

* cited by examiner

SPRING-LOADED BALLOON

PRIORITY

This continuation application claims the benefits of priority under 35 USC § 120 to prior U.S. patent application Ser. No. 14/706,058 filed May 7, 2015, of which the entirety of the prior application is incorporated by reference into this continuation application.

BACKGROUND OF THE INVENTION

1. Field of the Invention

This invention relates to medical devices. More particularly, this invention relates to improvements in cardiac catheterization.

2. Description of the Related Art

Cardiac arrhythmias, such as atrial fibrillation, occur when regions of cardiac tissue abnormally conduct electric signals to adjacent tissue, thereby disrupting the normal cardiac cycle and causing asynchronous rhythm.

Procedures for treating arrhythmia include surgically disrupting the origin of the signals causing the arrhythmia, as well as disrupting the conducting pathway for such signals. By selectively ablating cardiac tissue by application of energy via a catheter, it is sometimes possible to cease or modify the propagation of unwanted electrical signals from one portion of the heart to another. The ablation process destroys the unwanted electrical pathways by formation of non-conducting lesions.

Circumferential lesions at or near the ostia of the pulmonary veins have been created to treat atrial arrhythmias. U.S. Pat. Nos. 6,012,457 and 6,024,740, both to Lesh, disclose a radially expandable ablation device, which includes a radiofrequency electrode. Using this device, it is proposed to deliver radiofrequency energy to the pulmonary veins in order to establish a circumferential conduction block, thereby electrically isolating the pulmonary veins from the left atrium.

U.S. Pat. No. 6,814,733 to Schwartz et al., which is commonly assigned herewith and herein incorporated by reference, describes a catheter introduction apparatus having a radially expandable helical coil as a radiofrequency emitter. In one application the emitter is introduced percutaneously, and transseptally advanced to the ostium of a pulmonary vein. The emitter is radially expanded, which can be accomplished by inflating an anchoring balloon about which the emitter is wrapped, in order to cause the emitter to make circumferential contact with the inner wall of the pulmonary vein. The coil is energized by a radiofrequency generator, and a circumferential ablation lesion is produced in the myocardial sleeve of the pulmonary vein, which effectively blocks electrical propagation between the pulmonary vein and the left atrium.

Another example is found in U.S. Pat. No. 7,340,307 to Maguire, et al., which proposes a tissue ablation system and method that treats atrial arrhythmia by ablating a circumferential region of tissue at a location where a pulmonary vein extends from an atrium. The system includes a circumferential ablation member with an ablation element and includes a delivery assembly for delivering the ablation member to the location. The circumferential ablation member is generally adjustable between different configurations to allow both the delivery through a delivery sheath into the atrium and the ablative coupling between the ablation element and the circumferential region of tissue.

SUMMARY OF THE INVENTION

Commonly assigned copending application Ser. No. 14/578,807, which is herein incorporated by reference, describes how a balloon catheter may be injected with saline and used to ablate the ostium of a pulmonary vein. This and other applications of an improved balloon catheter are addressed herein.

In embodiments of the present invention a spring, and a flexible protective sleeve for the spring are inserted into the balloon. In the deflated (fully evacuated) state of the balloon, the spring is uncompressed and untwisted, and is in its resting state. The untwisted, uncompressed spring is configured to retain the deflated balloon around the spring, so that the deflated balloon arranges compactly and tidily about the spring.

The balloon is inflated by being injected with saline solution. The inflation forces the spring to compress and twist from its resting state. When the balloon is inflated the spring is in its compressed, twisted state and has torque. When the balloon is fully deflated, the spring is extended, untwisted and torsionless.

By incorporating a spring which both compresses and twists as described above, embodiments of the present invention enable the deflated balloon to be stored efficiently and neatly for delivery through a guiding sheath, while the inflated balloon is maintained in its correct inflated shape.

There is provided according to embodiments of the invention an ablation apparatus including a probe having a hollow shaft, a longitudinal axis and a distally disposed balloon assembly. The balloon assembly includes a spring having a resting axially elongated configuration and a torsed, axially shortened configuration. An inflatable balloon is mechanically linked to the spring. A flexible sheath is disposed about the spring within the balloon, the sheath and the wall of the balloon defining a chamber to contain a fluid flowing therein and thereout for inflation and deflation of the balloon. Inflation urges the spring into the torsed, axially shortened configuration and deflation permits the spring to return to the resting axially elongated configuration.

In one aspect of the apparatus includes proximal and distal couplers attached to the balloon and the sheath. The proximal and distal couplers are independently rotatable about the longitudinal axis of the probe.

According to yet another aspect of the apparatus, the proximal and distal couplers have a lumen for slidably receiving an extrusion therethrough.

According to still another aspect of the apparatus, at least one of the proximal and distal couplers has ports formed therein to establish fluid communication between the chamber and a fluid source via the shaft.

According to another aspect of the apparatus, in the resting axially elongated configuration the balloon is wrapped about the spring.

According to a further aspect of the apparatus, the balloon assembly is deployable through the steerable guiding sheath.

There is further provided according to embodiments of the invention a method which is carried out by inserting a probe having a hollow shaft, and a distally disposed balloon assembly into a heart of a subject. The balloon assembly includes a spring having a resting axially elongated configuration and a torsed axially shortened configuration, an inflatable balloon mechanically linked to the spring and enclosing the spring. The method is further carried out by urging the spring into the torsed axially twisted configuration by flowing a fluid into the chamber to thereby inflate the balloon, and deflating the balloon by removing the fluid from the chamber to allow the spring to assume the resting axially elongated configuration.

According to another aspect of the method, the balloon assembly also includes proximal and distal couplers attaching to the balloon.

According to an additional aspect of the method, the proximal and distal couplers are independently rotatable about the longitudinal axis.

According to still another aspect of the method, the proximal and distal couplers have a lumen for slidably receiving an extrusion therethrough.

According to yet another aspect of the method, at least one of the proximal and distal couplers has ports formed therein, and flowing a fluid is performed by passing the fluid between the chamber and a fluid source via the shaft.

According to a further aspect of the method, in the resting axially elongated configuration the balloon is wrapped about the spring, and inflating the balloon comprises unwrapping the balloon about the spring. Deflating the balloon comprises wrapping the balloon about the spring.

One aspect of the method includes deploying the balloon assembly through a steerable guiding sheath.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

System Description

Figure 1:
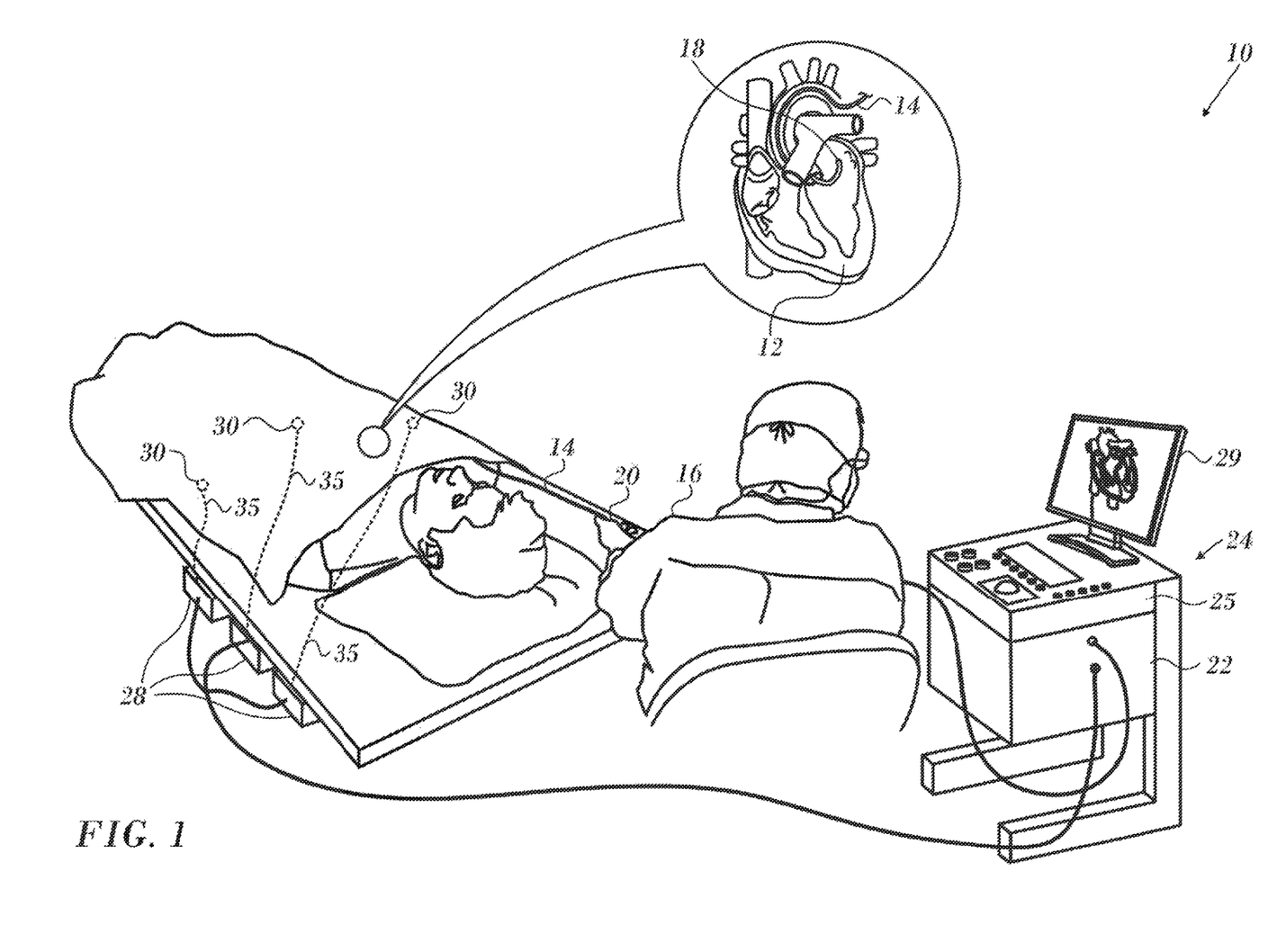
FIG. 1 is a pictorial illustration of a system for performing catheterization procedures on a heart, in accordance with a disclosed embodiment of the invention.

Turning now to the drawings, reference is initially made to FIG. 1, which is a pictorial illustration of a system 10 for evaluating electrical activity and performing ablative procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall, for example, at an ablation target site. Electrical activation maps may be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically above 60° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a processor 22, located in a console 24. The processor 22 may fulfill several processing functions as described below.

Wire connections 35 link the console 24 with body surface electrodes 30 and other components of a positioning sub-system for measuring location and orientation coordinates of the catheter 14. The processor 22 or another processor (not shown) may be an element of the positioning subsystem. Catheter electrodes (not shown) and the body surface electrodes 30 may be used to measure tissue impedance at the ablation site as taught in U.S. Pat. No. 7,536,218, issued to Govari et al., which is herein incorporated by reference. Temperature sensors (not shown), typically a thermocouple or thermistor, may be mounted on ablation surfaces on the distal portion of the catheter 14 as described below.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem is described in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by sensors such as electrical, temperature and contact force sensors, and a plurality of location sensing electrodes (not shown) located distally in the catheter 14. The digitized signals are received and used by the console 24 and the positioning system to compute the position and orientation of the catheter 14, and to analyze the electrical signals from the electrodes.

In order to generate electroanatomic maps, the processor 22 typically comprises an electroanatomic map generator, an image registration program, an image or data analysis program and a graphical user interface configured to present graphical information on the monitor 29.

Typically, the system 10 includes other elements, which are not shown in the figures for the sake of simplicity. For example, the system 10 may include an electrocardiogram (ECG) monitor, coupled to receive signals from one or more body surface electrodes, in order to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided. The system 10 may receive image data from an external imaging modality, such as an MRI unit or the like and includes image processors that can be incorporated in or invoked by the processor 22 for generating and displaying images.

Balloon Assembly

Figure 2:
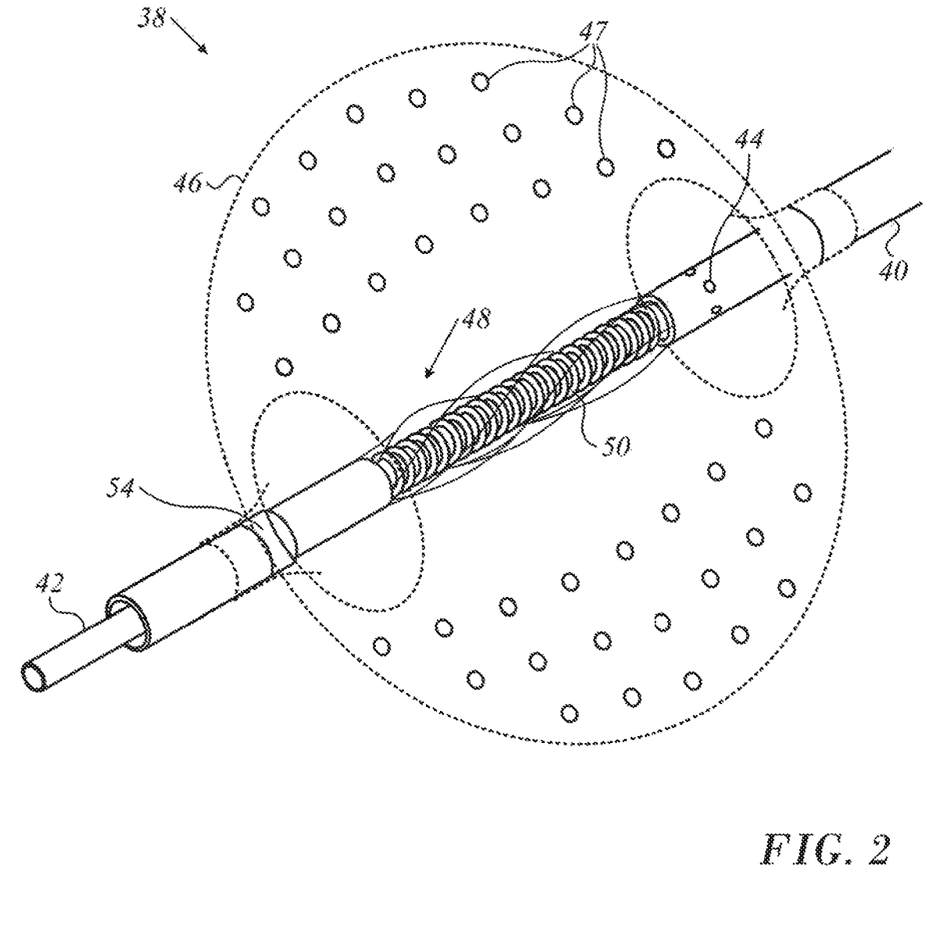
FIG. 2 is a view of the distal portion of the catheter shown in FIG. 1 in accordance with an embodiment of the invention.

Reference is now made to FIG. 2, which is an oblique view of the distal portion of a balloon assembly 38 at the distal end of shaft 40 of catheter 14 in accordance with an embodiment of the invention, in accordance with an embodiment of the invention. Extending through the lumen of the shaft 40 and protruding beyond the tip is a flexible polymer extrusion 42. The extrusion 42 may be used for device access, for example a guidewire to assist in introducing the catheter. Ports 44 are provided for irrigation and for inflation of a polymer balloon 46. The fluid is allowed to exit the inflated balloon through small pores 47

A spring mechanism 48 comprises a piston-type coaxial compression spring 50, overlying the extrusion 42, is attached to the shaft 40 by couplers 52, 54. The spring 50 is rigidly bonded to the proximal and distal ends of the balloon 46 or to the couplers 52, 54. A flexible sleeve 56 connected to the couplers 52, 54 is enclosed by the balloon 46. The sleeve 56 surrounds the spring 50 and prevents fluid in a chamber defined by the outer wall of the sleeve 56 and the inner wall of the balloon 46 from escaping through the interstices of the spring 50.

During manufacture, while the spring 50 is in its home position, and not influenced by external forces, the proximal end of the balloon 46 is secured to the proximal end of the balloon assembly 38 or the coupler 52. The balloon 46 is then stretched axially by about 1 cm, and twisted axially (about one-half to one full twist) before being secured to the distal end of the balloon assembly 38 or the coupler 54. When the balloon 46 is inflated, internal fluid pressure causes it to untwist and to shorten axially by about 1 cm. Since the balloon 46 is mechanically linked to the balloon 46, an angular force is transmitted by the untwisting balloon through the couplers 52, 54 to the spring 50, thereby producing torsion upon and compressing the spring 50. As a result the spring 50 transitions from a resting axially elongated configuration into a torsed, axially shortened configuration, and the entire balloon assembly 38 becomes axially shortened and the balloon becomes radially enlarged.

Figure 3:
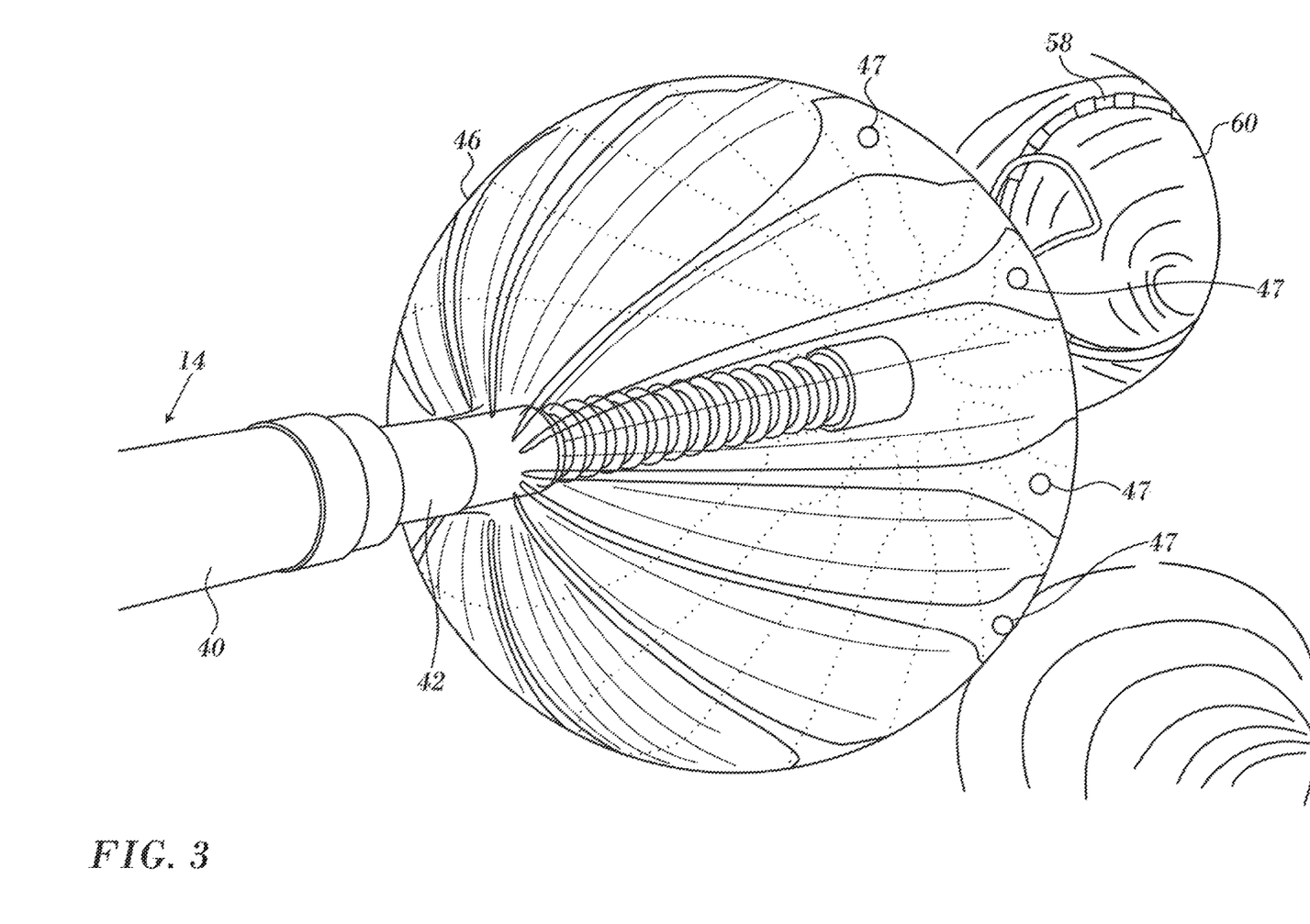
FIG. 3 is another view of the distal portion of the catheter shown in FIG. 1 in accordance with an embodiment of the invention.

Reference is now made to FIG. 3 which is a view of the distal portion of the catheter 14 (FIG. 1) in accordance with an embodiment of the invention. A lasso guide 58 has been deployed through the catheter 14 and is engaged with the wall of pulmonary vein 60. Balloon 46 has been inflated, and is stabilized by the lasso guide 58 that is anchored against the vessel wall. Correct placement of the balloon 46 in the pulmonary vein 60 can be verified by injecting a contrast agent through the catheter 14. Additionally or alternatively the contrast agent may be injected into the balloon 46. The balloon 46 may be provided with electrodes 62 as taught in the above noted application Ser. No. 14/578,807, The electrodes 62 can be used for mapping or ablation.

Figure 4:
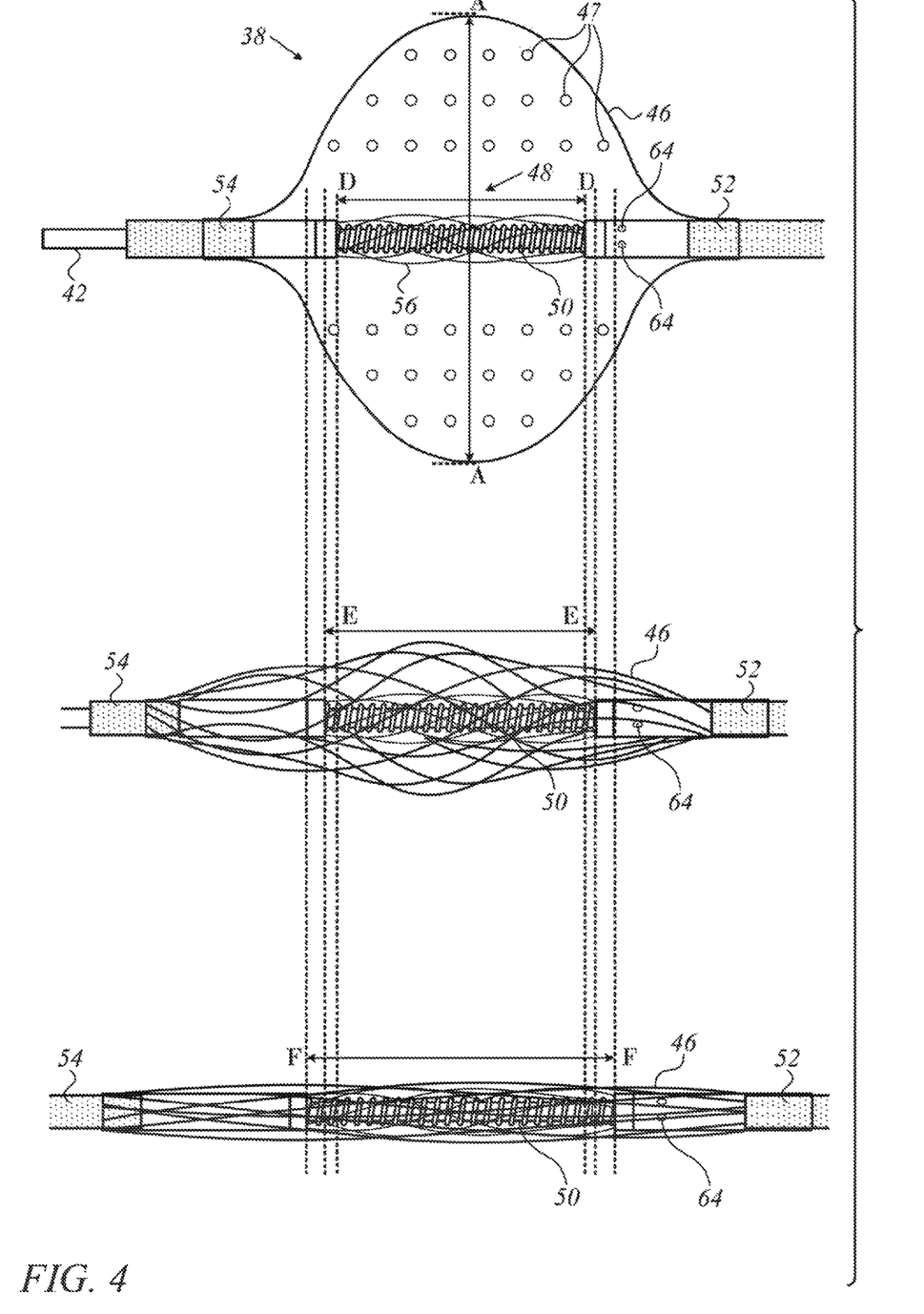
FIG. 4 is a pictorial series of three side elevations of a balloon assembly in accordance with an embodiment of the invention.

Reference is now made to FIG. 4, which is a pictorial series of three side elevations of the balloon assembly 38 in various phases of inflation and deflation in accordance with an embodiment of the invention. The balloon 46 and spring mechanism 48 are enabled by the couplers 52, 54 to slide over and rotate freely and independently with respect to one another about the extrusion 42, i.e., about the longitudinal axis of the catheter. The balloon 46 is inflated by pressure exerted by fluid entering the balloon 46 through pores 64. The expanding balloon shortens along its longitudinal axis but increases in transverse diameter (line AA). In the uppermost image the balloon 46 is fully inflated. As a result of internal fluid pressure and consequent deformation of the balloon, the spring 50 is urged into a fully compressed and maximally torsed state, effectively shortening its length dimension (D-D).

In the middle image release of the internal fluid pressure, e.g., by a valve (not shown), has allowed the balloon 46 to partially deflate, aided by the restorative force of the spring 50. The spring 50 attempts to return to its resting state by lengthening, untwisting and opposing the internal fluid pressure in the balloon 46, thereby aiding the fluid to escape through the pores 64. Additionally or alternatively the fluid may escape through pores 47, In the middle image, the spring 50 is partially untwisted, and its length dimension (line E-E) is larger than its length dimension (line D-D) in the uppermost image.

In the lowermost image, the balloon 46 is fully deflated and the balloon assembly 38 fully collapsed. In this configuration the balloon assembly 38 can be introduced through the lumen of a catheter and withdrawn upon completion of a medical procedure. The spring 50 is in a resting state, fully extended and exerting no torsion on the mechanism. Its length dimension (F-F) is maximal relative to the length dimensions D-D, E-E.

Figure 5:
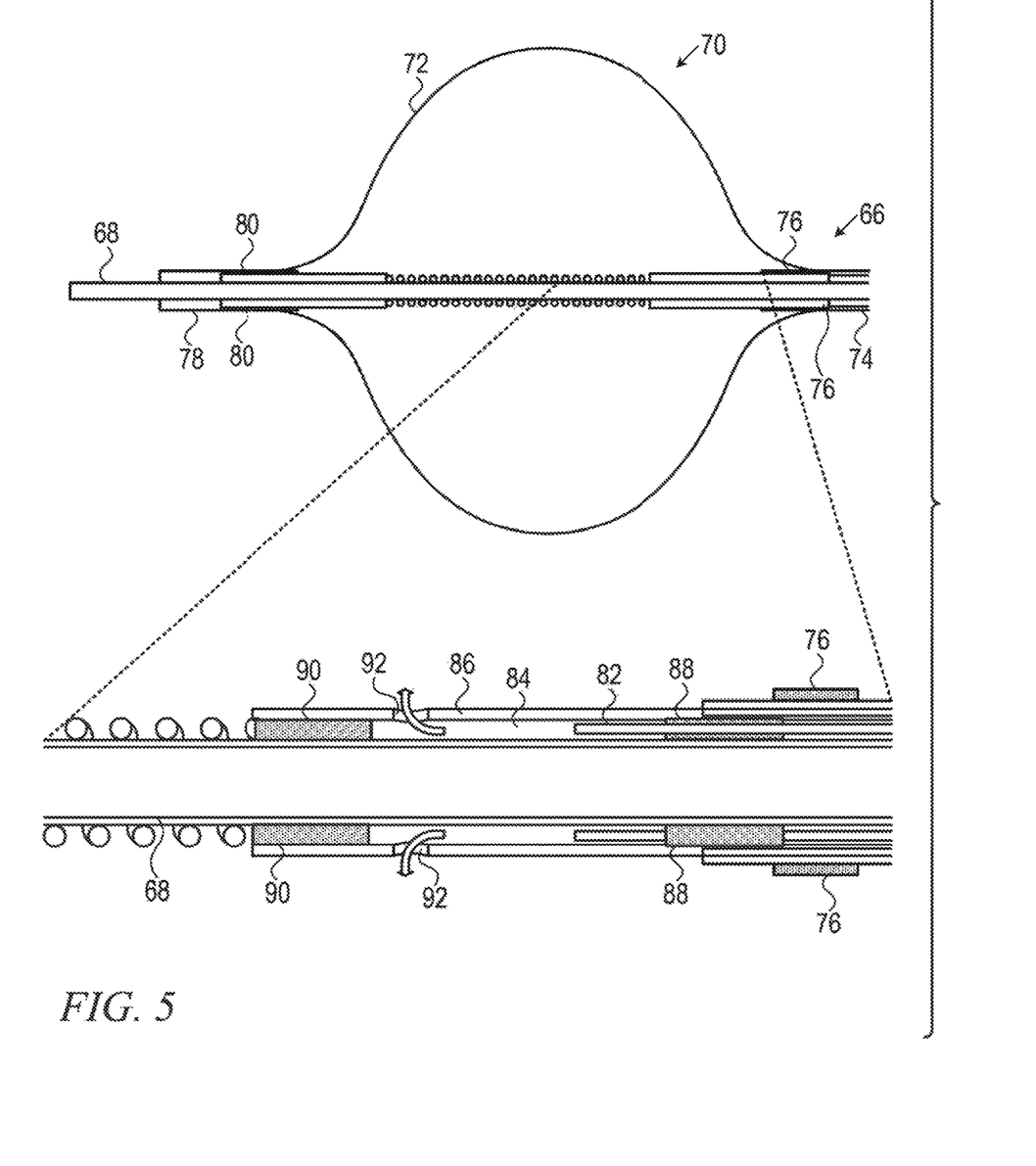
FIG. 5 is a sectional view through the longitudinal axis of a probe in accordance with an embodiment of the invention.

Reference is now made to FIG. 5, which is a sectional view through the longitudinal axis of a probe 66, in accordance with an embodiment of the invention. A hollow inner shaft 68 extends through the lumen of the probe 66. Its functions are to support balloon assembly 70 and to provide ingress for a guidewire (not shown). Balloon 72 is adhered to a proximal section 74 of the probe 66 by a circumferential seal 76. The balloon 72 adheres to a discontinuous distal section 78 by circumferential seal 80. A lumen 82 leads into a manifold 84 that is defined by the outer surface of the shaft 68, the inner surface 86 of the probe 66 and by seals 88, 90. Pores 92 allow communication for fluid flowing through the lumen 82 and the manifold 84 to inflate and deflate the balloon 72.

Figure 6:
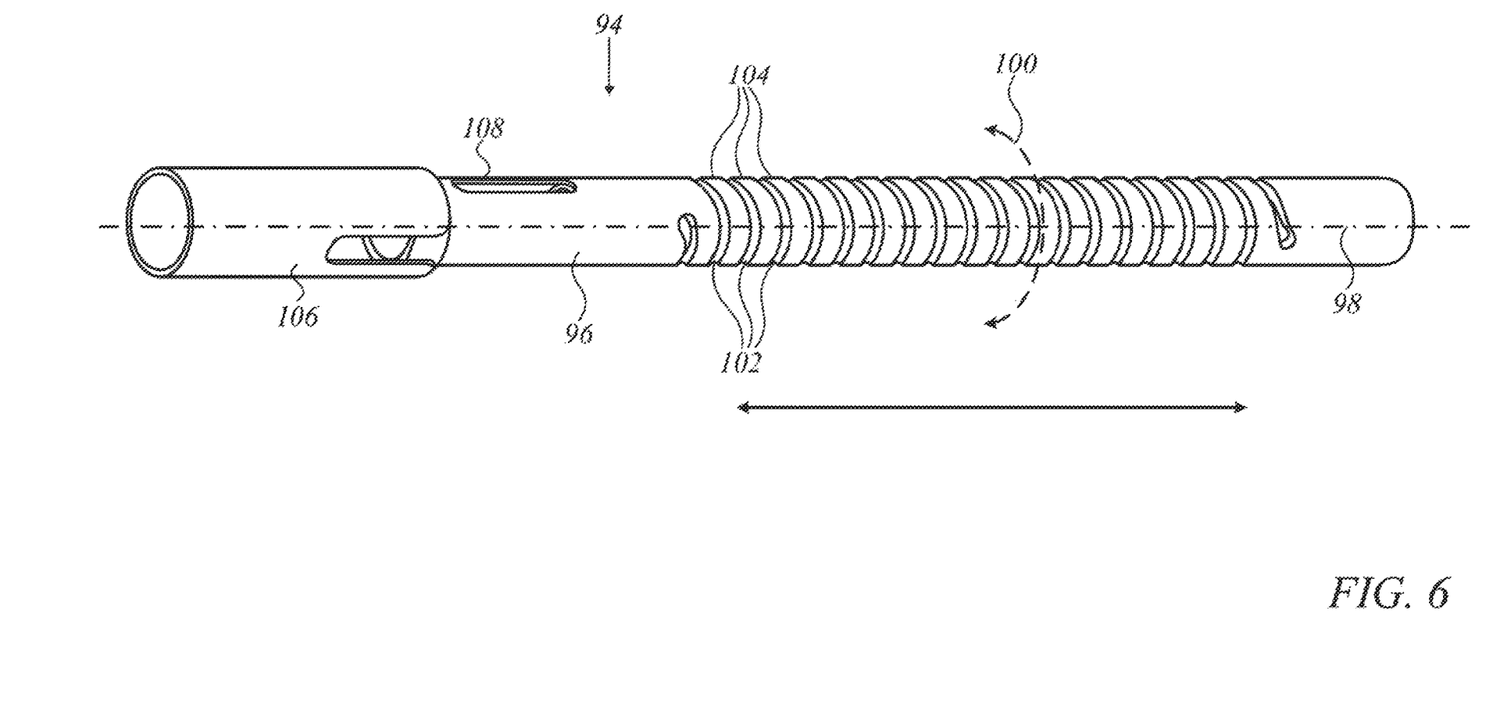
FIG. 6 is an elevation of a spring, which is incorporated in a balloon assembly in accordance with an embodiment of the invention.

Reference is now made to FIG. 6, which is an elevation of the spring 94, which is incorporated in a balloon assembly in accordance with an embodiment of the invention. The spring 94 may be made of a resilient plastic material such as PEEK™ or metal such as nitinol or stainless steel. The spring 94 has a shaft 96 that may be twisted and untwisted about its longitudinal axis 98, as shown by arrow 100, so that the spring alternates between a relaxed elongated state and a torsed, compressed state. When transitioning into the compressed state interstices 102 that separate coils 104 become narrow, and the spring 94 shortens on the longitudinal axis 98. A coupler 106 is attached to the shaft 96 aby either by a weld, to form one integral unit, or by other means. One of couplers is omitted in FIG. 6. A longitudinal slot 108 is formed in the shaft 96. It provides a port to route the saline into the balloon.

Operation

Figure 7:
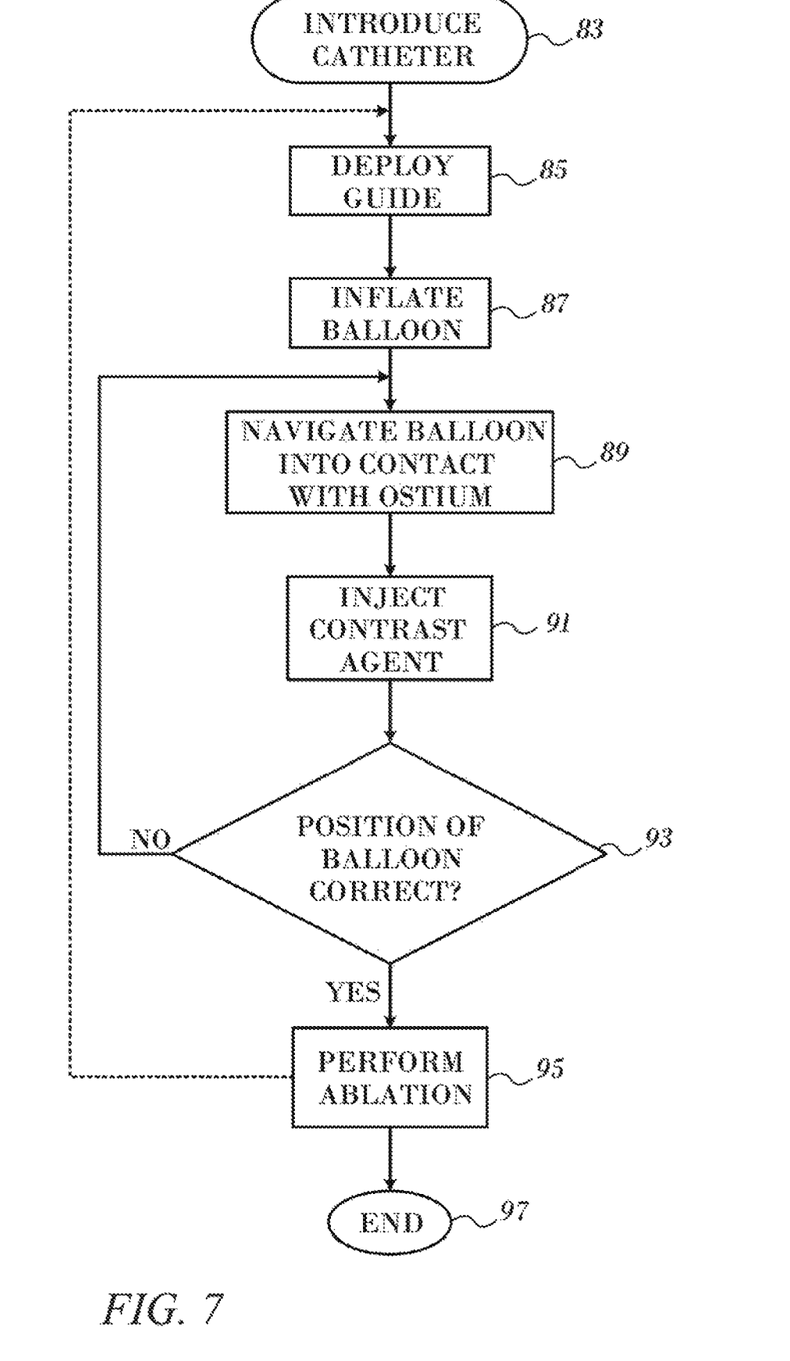
FIG. 7 is a flow-chart of a method of cardiac catheterization in accordance with an embodiment of the invention.

Reference is now made to FIG. 7, which is a flow-chart of a method of cardiac catheterization using a balloon catheter in accordance with an embodiment of the invention. This example concerns operations at the pulmonary vein ostia; however, the method is applicable, mutatis mutandis, to other structures and procedures in the heart. The process steps are shown in a particular linear sequence for clarity of presentation. However, it will be evident that many of them can be performed in parallel, asynchronously, or in different orders. Moreover, not all illustrated process steps may be required to implement the method. The method is disclosed for clarity of exposition with reference to the preceding figures, but is applicable to other embodiments and configurations of the balloon assembly as well.

At initial step 83 a cardiac catheter is conventionally introduced into the left atrium of a heart. A guiding sheath may be employed to deploy the lasso guide and balloon. The Destino™ 12-F steerable guiding sheath is suitable for this purpose.

Next, at step 85 a lasso guide is deployed and positioned to engage the interior wall of a pulmonary vein. At this stage the spring 50 in the balloon assembly 38 is fully extended and in an untorsioned state. The balloon 46 and sleeve 56 are wrapped about and collapsed to their maximum extent. When the balloon 46 is fully inflated, the spring 50 is compressed and fully twisted with respect to its initial position.

Next, at step 87 the balloon is extended over the lasso guide and inflated by causing a fluid flow through the ports 44 into a chamber that is defined by the inner wall of the balloon 46 and the sleeve 56. As inflation occurs, saline enters the balloon 46 through the ports 44. The spring 50 compresses and twists, in opposition to forces exerted by the expanding balloon.

Next, at step 89 the balloon is navigated into circumferential contact with a pulmonary vein ostium in order to occlude the ostium.

Next, at an optional step 91 a radio-opaque contrast agent is injected through the lumen of the catheter and through appropriate irrigation ports of the catheter into the pulmonary vein in order to confirm that the balloon is in a correct position against the pulmonary vein ostium. The contrast agent does not enter the balloon.

Control now proceeds to decision step 93, where it is determined if the balloon is correctly positioned. If the determination at decision step 93 is negative, then control returns to step 89 and another attempt is made to position the balloon.

If the determination at decision step 93 is affirmative then control proceeds to step 95 where a medical procedure, e.g., mapping or ablation is performed using appropriate ablation electrodes on the catheter.

After completion of the ablation, the procedure may be iterated using another pulmonary vein ostium by withdrawal of the balloon and the lasso guide 58. Control may then return to step 85. Alternatively, the procedure may end by removal of the catheter at final step 97. Prior to removal of the catheter the balloon is deflated. Referring again to FIG. 4, the procedure is essentially a reversal of the inflation procedure, and assisted by the action of the spring 50, which extends and untwists, thereby assisting the balloon to compress and fold about the spring 50 and the underlying shaft, e.g., extrusion 42. The fluid contents of the balloon 46 leave the balloon through pores 47.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. An ablation apparatus comprising:
   a probe extending along a longitudinal axis and having a distally disposed balloon assembly, the balloon assembly comprising:
   a spring having an uncompressed torsionless configuration and a compressed, axially shortened configuration;
   a balloon mechanically linked to the spring and enclosing the spring, the balloon having a wall provided with electrodes for mapping or ablation, the wall having pores to allow a fluid to exit the balloon; and
   a flexible sheath disposed about the spring within the balloon, the sheath and the wall of the balloon defining a chamber to contain a fluid flowing therein to the balloon and out through the pores, wherein the balloon becomes radially enlarged when the spring is in the compressed, axially shortened configuration and the balloon becomes collapsed when the spring returns to the uncompressed torsionless configuration.

2. The apparatus according to claim 1, further comprising proximal and distal couplers attaching to the balloon and the sheath.

3. The apparatus according to claim 2, wherein the proximal and distal couplers are independently rotatable about the longitudinal axis.

4. The apparatus according to claim 2, wherein the proximal and distal couplers have a lumen for slidably receiving an extrusion therethrough, the proximal and distal couplers being rotatable about the extrusion.

5. The apparatus according to claim 2, wherein at least one of the proximal and distal couplers has ports formed therein to establish fluid communication between the chamber and a fluid source via a hollow shaft coupled to the probe.

6. The apparatus according to claim 1, wherein the balloon is wrapped about the spring in the uncompressed configuration of the spring.

7. The apparatus according to claim 1, wherein the balloon assembly is deployable through a steerable guiding sheath.

8. A method of mapping or ablating biological tissues, the method comprising the steps of:
- inserting a probe extending along a longitudinal axis and having a distally disposed balloon assembly into tissues of a subject, the balloon assembly comprising
  - a spring having a torsionless extended configuration and a compressed configuration, and a balloon linked to the spring and having a wall provided with electrodes for mapping or ablating, the wall having pores to allow fluid to exit the balloon;
- urging the spring into the compressed configuration to radially enlarge the balloon;
- mapping or ablating the tissues with the electrodes on the balloon; and
- allowing the spring to assume the torsionless extended configuration to collapse the balloon.

9. The method according to claim 8, wherein the balloon assembly further comprises proximal and distal couplers attached to the balloon.

10. The method according to claim 9, wherein the proximal and distal couplers are independently rotatable about the longitudinal axis.

11. The method according to claim 9, wherein the proximal and distal couplers have a lumen for slidably receiving an extrusion therethrough.

12. The method according to claim 9, wherein at least one of the proximal and distal couplers has ports formed therein, and flowing a fluid is performed by passing the fluid from a fluid source via a hollow shaft coupled to the probe.

13. The method according to claim 8, wherein in the torsionless extended configuration of the spring, the balloon is wrapped about the spring, and in the radially enlarged configuration of the balloon includes unwrapping the balloon about the spring.

14. The method according to claim 8, wherein collapsing the balloon comprises wrapping the balloon about the spring in the torsionless extended configuration of the spring.

15. The method according to claim 8, further comprising deploying the balloon assembly through a steerable guiding sheath.

* * * * *